US011482808B2

(12) United States Patent
Jagminas et al.

(10) Patent No.: US 11,482,808 B2
(45) Date of Patent: Oct. 25, 2022

(54) MEDICAL IMAGING DEVICE CONNECTOR ASSEMBLY

(71) Applicant: KONINKLIJKE PHILIPS N.V., Eindhoven (NL)

(72) Inventors: Eugenijus Jagminas, Wakefield, MA (US); Sujith Kanakasabhapathi, Acton, MA (US); Oliver Naumovski, Eindhoven (NL); Satish Sanjay Singh, Everett, MA (US); Michael J Wight, Stoneham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 398 days.

(21) Appl. No.: 16/630,599

(22) PCT Filed: Jul. 9, 2018

(86) PCT No.: PCT/EP2018/068486
§ 371 (c)(1),
(2) Date: Jan. 13, 2020

(87) PCT Pub. No.: WO2019/011830
PCT Pub. Date: Jan. 17, 2019

(65) Prior Publication Data

US 2020/0176922 A1 Jun. 4, 2020

Related U.S. Application Data

(60) Provisional application No. 62/531,386, filed on Jul. 12, 2017.

(51) Int. Cl.
*H01R 13/52* (2006.01)
*A61B 1/00* (2006.01)
(Continued)

(52) U.S. Cl.
CPC ..... *H01R 13/5224* (2013.01); *A61B 1/00124* (2013.01); *A61B 8/4433* (2013.01);
(Continued)

(58) Field of Classification Search
CPC ............ H01R 13/5224; H01R 13/5221; H01R 13/5219; H01R 13/193; H01R 13/512;
(Continued)

(56) References Cited

U.S. PATENT DOCUMENTS 5,477,858 A * 12/1995 Norris ................ G01S 7/52069 600/455
5,630,419 A 5/1997 Ranalletta
(Continued)

FOREIGN PATENT DOCUMENTS

GB 2321789 A 8/1998

OTHER PUBLICATIONS

International Search Report and Written Opinion for International Application No. PCT/EP2018/068486, filed Jul. 9, 2018, 13 pages.

*Primary Examiner* — Harshad C Patel

(57) ABSTRACT

A medical imaging device connector assembly for connecting a medical imaging device to a terminal of a medical imaging system is provided. The medical imaging device connector assembly includes a top housing having a first base cutout; a bottom housing configured to couple to the top housing, the bottom housing including a second base cutout; a base housing positioned within the first and second base cutouts; a plurality of printed circuit boards (PCBs) disposed between the top housing and the bottom housing; an electrical connector positioned within the base housing; and an elastic seal member surrounding a circumference of the base housing. When the top housing is coupled to the bottom housing, the elastic seal member is compressed by the plurality of PCBs in a first direction and by the top and
(Continued)

bottom housings in a second direction perpendicular to the first direction to prevent fluid ingress.

17 Claims, 8 Drawing Sheets

(51) Int. Cl.
*A61B 8/00* (2006.01)
*H01R 13/193* (2006.01)
*H01R 13/512* (2006.01)
*H01R 13/66* (2006.01)
*A61B 8/12* (2006.01)

(52) U.S. Cl.
CPC ......... *H01R 13/193* (2013.01); *H01R 13/512* (2013.01); *H01R 13/5202* (2013.01); *H01R 13/665* (2013.01); *A61B 8/12* (2013.01)

(58) Field of Classification Search
CPC .... H01R 13/506; H01R 13/508; H01R 13/46; H01R 13/52; H01R 13/5202; H01R 13/523; H01R 13/533; H01R 13/665; H01R 13/6658; H01R 13/6675; A61B 8/4433; A61B 8/44; A61B 8/4405; A61B 8/4411; A61B 8/4416; A61B 8/4427; A61B 8/12
USPC .......................................................... 600/132
See application file for complete search history.

(56) References Cited

U.S. PATENT DOCUMENTS

| | | | | |
|---|---|---|---|---|
| 5,678,551 | A | 10/1997 | Stevens | |
| 5,865,733 | A * | 2/1999 | Malinouskas | A61B 8/4209 128/903 |
| 6,117,084 | A * | 9/2000 | Green | A61B 8/00 600/459 |
| 6,561,979 | B1 | 5/2003 | Wood et al. | |
| 7,862,380 | B1 * | 1/2011 | Wang | H01R 13/52 439/694 |
| 7,891,230 | B2 * | 2/2011 | Randall | G01M 3/3272 73/1.82 |
| 7,967,617 | B2 * | 6/2011 | Vonnegut | H01R 13/6658 439/142 |
| 8,147,272 | B2 * | 4/2012 | Rhein | H01R 13/5202 439/556 |
| 8,246,383 | B2 | 8/2012 | Schmidt et al. | |
| 8,513,554 | B2 * | 8/2013 | Peng | H01H 9/0228 200/332.1 |
| 8,574,001 | B2 * | 11/2013 | Lee | H01R 13/7172 439/271 |
| 8,840,430 | B2 * | 9/2014 | Bausch | H01R 13/5219 439/587 |
| 9,306,313 | B2 * | 4/2016 | Heggemann | H01R 13/74 |
| 9,363,343 | B2 * | 6/2016 | Rao | H04B 1/3888 |
| 9,478,998 | B1 * | 10/2016 | Lapetina | H01R 24/62 |
| 9,509,084 | B2 * | 11/2016 | Zhao | H01R 43/005 |
| 9,991,625 | B2 * | 6/2018 | Ozaki | H01R 13/73 |
| 2005/0245132 | A1 * | 11/2005 | Huang | H01R 13/6275 439/607.04 |
| 2007/0207668 | A1 * | 9/2007 | Masuzaki | G02B 6/3891 439/587 |
| 2009/0191927 | A1 * | 7/2009 | Hong | H04M 1/0274 455/575.8 |
| 2016/0007957 | A1 | 1/2016 | Murphy et al. | |
| 2016/0268736 | A1 | 9/2016 | Goto et al. | |

* cited by examiner

MEDICAL IMAGING DEVICE CONNECTOR ASSEMBLY

RELATED APPLICATIONS

This application is the U.S. National Phase application under 35 U.S.C. § 371 of International Application No. PCT/EP2018/068486, filed on Jul. 9, 2018, which claims the benefit of Provisional Application No. 62/531,386, filed Jul. 12, 2017. These applications are hereby incorporated by reference herein.

TECHNICAL FIELD

The present disclosure relates generally to medical imaging and, in particular, to connector assemblies of a medical imaging device. For example, an ultrasound imaging device connector assembly can include a front housing configured to be secured to a front internal frame and a back housing configured to be secured to a back internal frame.

BACKGROUND

Medical imaging devices are widely used as a diagnostic tool for internally or externally assessing physiology to determine the need for treatment and assessing the effectiveness of the treatment. When in use, the medical imaging device is in contact with tissue and/or fluids of the patient, saline solution, ultrasound gel, and/or other substances which render the imaging device non-sterile. In the case of re-usable devices, upon conclusion of the imaging, the medical imaging device is disinfected with use of enzymatic cleaners and disinfectants before it can be used again. In some instances, the medical imaging device is sterilized within an autoclave. The imaging device, along with a cable and a connector assembly connected thereto, are therefore exposed to a highly humid environment. The electrical connectors and printed circuit boards inside the connector assemblies are especially prone to failure due to ingress of enzymatic cleaners, disinfectants, bodily fluids, saline solutions, ultrasound gel, and/or or to exposure to the humid environment.

While the existing connector assemblies of medical imaging devices generally attempt to prevent ingress of fluids during operation and sterilization, they are not satisfactory in all aspects. There is a need for a medical imaging device with a connector assembly that can better protect electrical circuitry and connectors therein from fluid ingress.

SUMMARY

Embodiments of the present disclosure provide a medical imaging device connector assembly for connecting a medical imaging device to a terminal of a medical imaging system. The medical imaging device connector assembly includes a top housing having a first base cutout, a bottom housing having a second base cutout, a base housing positioned within the first and second base cutouts, a plurality of printed circuit boards (PCBs) disposed between the top housing and the bottom housing, an electrical connector positioned within the base housing, and an elastic seal member surrounding a circumference of the base housing. When the top housing is coupled to the bottom housing, the elastic seal member is compressed by the plurality of PCBs in a first direction and by the top and bottom housings in a second direction perpendicular to the first direction prevents fluid from entering an interface between the base housing, on the one hand, and the coupled top and bottom housings, on the other hand. In some embodiments, the top housing comprises an internal surface and a boss coupled to the internal surface of the top housing and the bottom housing comprises an internal surface and a boss coupled to the internal surface of the bottom housing. The boss on the top housing and the boss on the bottom housing engage and strain the elastic seal member.

In one embodiment, the present disclosure provides a medical imaging device connector assembly for connecting a medical imaging device to a terminal of a medical imaging system. The medical imaging device connector assembly includes a top housing having a first base cutout; a bottom housing configured to couple to the top housing, the bottom housing having a second base cutout; a base housing positioned within the first and second base cutouts; a plurality of printed circuit boards (PCBs) disposed between the top housing and the bottom housing; an electrical connector positioned within the base housing; and an elastic seal member surrounding a circumference of the base housing. When the top housing is coupled to the bottom housing, the elastic seal member is compressed by the plurality of PCBs in a first direction and by the top and bottom housings in a second direction perpendicular to the first direction to prevent fluid ingress. In some instances, the top housing is coupled to the bottom housing by at least a first screw and a second screw. In some instances, the elastic seal member includes a first through hole sized and shaped to receive the first screw and a second through hole sized and shaped to receive the second screw. In some implementations, the elastic seal member includes a top edge configured to engage the top housing and a bottom edge configured to engage the bottom housing.

In some embodiments, the base housing includes two short sides and two long sides and the elastic seal member includes a first lip parallel and adjacent to one short side and a second lip parallel and adjacent to the other short side. Each of the first and second lips is configured to engage the top and the bottom housings simultaneously. In some instances, the medical imaging device connector assembly further includes a gasket. The top housing includes a first groove configured to receive a portion of the gasket and the bottom housing includes a second groove configured to receive a portion of the gasket, such that the gasket is disposed between the first groove and the second groove when the top housing is secured to the bottom housing. In some embodiments, the elastic seal member extends along a first plane having a first normal direction and the gasket extends along a second plane having a second normal direction, the first normal direction being perpendicular to the second normal direction. In some instances, the elastic seal member comprises conductive particles.

In some embodiments, the electrical connector of the medical imaging device connector assembly is a zero insertion force (ZIF) connector. In some implementations, the electrical connector is a female ZIF connector configured to be electrically connected to a male ZIF connector. In those implementations, the terminal of the medical imaging system includes the male ZIF connector.

In some embodiments, the medical imaging device connector assembly further includes a conical cable housing having a proximal end and a distal end. The proximal end has first outer diameter and the distal end has a second outer diameter smaller than the first outer diameter. In some implementations, the conical cable housing includes another gasket. For clarity, this gasket is sometimes referred to as the second gasket while the gasket disposed between the top and bottom housing is sometimes referred to as the first gasket. The second gasket includes a first extension and a second extension extending from the proximal end of the conical cable housing. In some instances, when the top housing is coupled to the bottom housing, the first and second extensions of the second gasket engage the first gasket. In some embodiments, top housing of the medical imaging device connector assembly includes an internal surface and a boss coupled to the internal surface of the top housing and the bottom housing includes an internal surface and a boss coupled to the internal surface of the bottom housing. The boss on the top housing and the boss on the bottom housing engage and strain the elastic seal member.

The present disclosure also provides a system. The system includes a medical imaging device. The medical imaging device includes a flexible elongate member comprising a proximal portion and a distal portion; an imaging assembly at the distal portion; and a connector assembly at the proximal portion and configured to connect to a terminal of a medical imaging system. The connector assembly includes a top housing including a first base cutout; a bottom housing configured to couple to the top housing, the bottom housing including a second base cutout; a base housing positioned within the first and second base cutouts; a plurality of printed circuit boards (PCBs) disposed between the top housing and the bottom housing; an electrical connector positioned within the base housing; and an elastic seal member surrounding a circumference of the base housing. When the top housing is coupled to the bottom housing, the elastic seal member is compressed by the plurality of PCBs in a first direction and by the top and bottom housings in a second direction perpendicular to the first direction to prevent fluid ingress. In some embodiments, the system further includes the medical imaging system.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
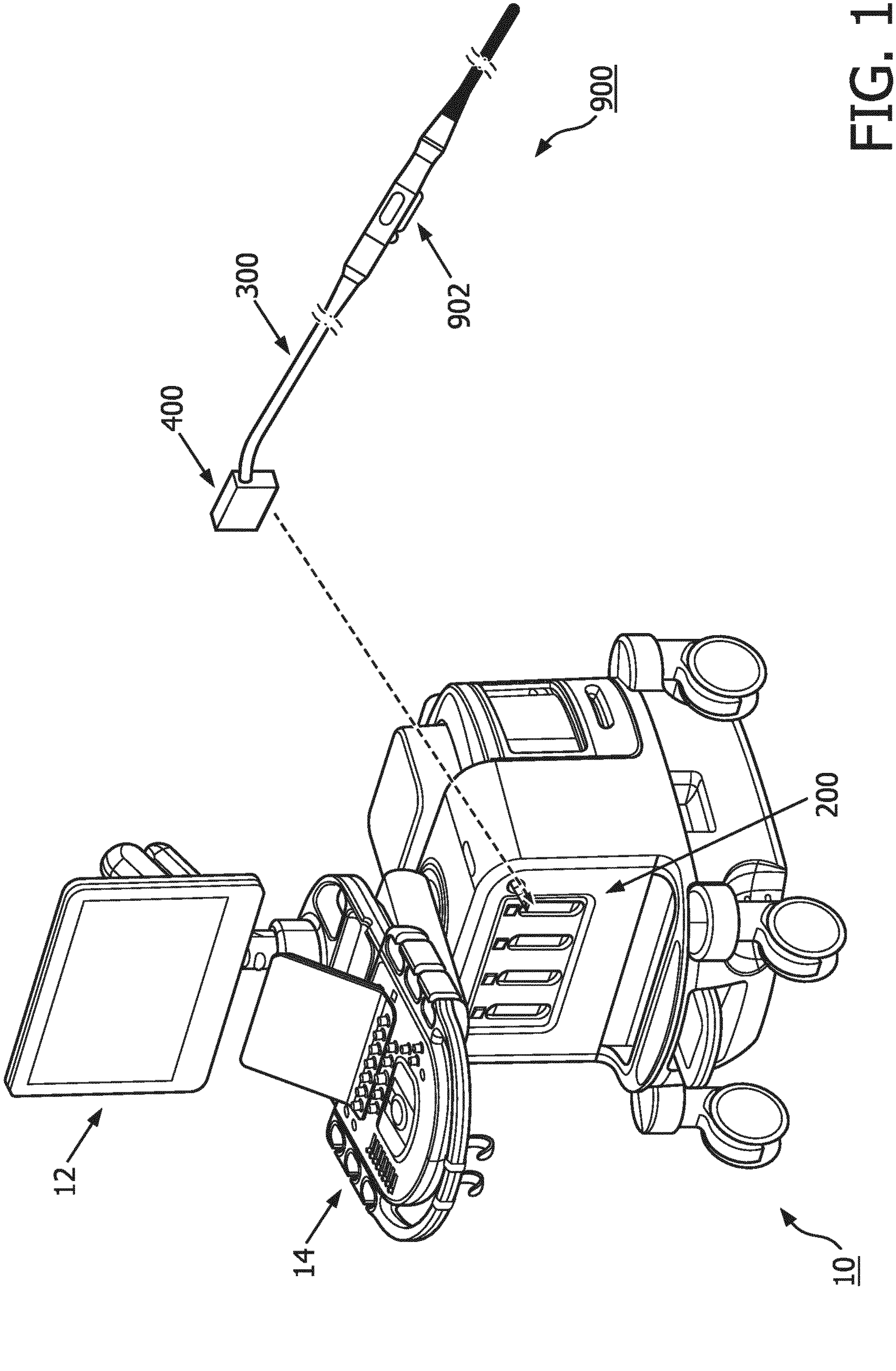
FIG. 1 is a diagrammatic perspective view of a medical imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic perspective view of a medical imaging system 10, according to aspects of the present disclosure. A medical imaging device 900 is connected to a cable 300 coupled to a connector assembly 400. In various embodiments, the medical imaging device 900 can be an ultrasound imaging device, a transesophageal echocardiography (TEE) probe, an endoscope, and/or other suitable devices. A distal portion of the medical imaging device 900 includes an imaging assembly 902. For example, the imaging assembly 902 can include a probe and one or more imaging elements. For example, the imaging elements can be ultrasound transducers, and the imaging assembly 902 can include one or more ultrasound transducer arrays. A proximal portion of the medical imaging device 900 includes the connector assembly 400. The cable 300 extends between the imaging assembly 902 and the connector assembly 400. In some instances, the cable 300 can be referenced as a flexible elongate member.

In some embodiments, the medical imaging device 900 is sized and shaped for positioning within the body of the patient, such as within the esophagus, heart, blood vessel, and/or other body lumen or cavity of the patient. In some embodiments, the medical imaging device 900s is sized and shaped to be positioned on the outside of the body, such as with the imaging assembly 902 in contact with the skin of the patient. The shape of the medical imaging device 900 shown in FIG. 1 is only for illustration purposes and does not in any way limit the shape of the medical imaging device according to aspects of the present disclosure.

In operation, the imaging assembly 902 can obtain imaging data associated with the body of the patient. Electrical signals representative of the imaging data can be transmitted from the imaging assembly 902 to the connector assembly 400 along one or more electrical conductors of the cable 300. The connector assembly 400 can be in mechanical and/or electrical communication with the medical imaging system 10, such that the electrical signals are transmitted from connector assembly 400 to the medical imaging system 10. The system 10 includes one or more processors and/or memory forming a processing circuit that can process the electrical signals and output a graphical representation of the imaging data on a display device 12. The one or more electrical conductors of the cable 300 and/or the connector assembly 400 facilitate communication between the medical imaging system 10 and the medical imaging device 900. For example, a user of the system 10 can control imaging using the medical imaging device 900 via a control interface 14 of the system 10. Electrical signals representative of commands from the system 10 can be transmitted to the medical imaging device 900 via the connector assembly 400 and/or the one or more conductors of the cable 300.

The connector assembly 400 is configured to be insertable into a slot or terminal 200 on the medical imaging system 10. Generally, the connector assembly 400 and the slot 200 can include any suitable connections that are configured to mechanically and/or electrically couple to one another. In some embodiments, the connector assembly 400 houses one or more male or female zero insertion force (ZIF) connectors. In such embodiments, the slot 200 includes corresponding female or male ZIF connectors. That way, when the connector assembly 400 is inserted into the slot 200, the male/female connectors in the connector assembly 400 are electrically connected to the female/male connectors in the slot 200. In other embodiments, the connector assembly 400 houses one or more low insertion force (LIF) connectors, flat flexible connectors (FFCs), ribbon cable connectors, and serial advanced technology attachment (SATA) connectors. In those embodiments, the slot 200 includes one or more corresponding connectors.

Figure 2:
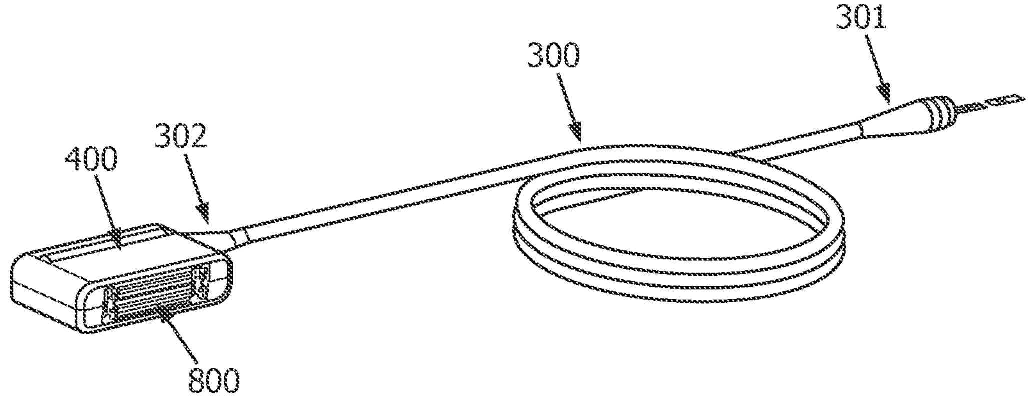
FIG. 2 is a diagrammatic perspective view of a connector assembly and a cable, according to aspects of the present disclosure.

FIG. 2 is a diagrammatic perspective view of a connector assembly 400 and a cable 300, according to aspects of the present disclosure. The cable 300 has a distal end 301 that is connected to the imaging assembly 902 (FIG. 1) and a proximal end 302 that is connected to the connector assembly 400. The cable 300 can include one or more electrical conductors and a conduit surrounding electrical conductors. In some embodiments, the connector assembly 400 includes one or more electrical connectors 800. In the embodiment shown in FIG. 2, the one or more electrical connectors 800 are two female ZIF connectors. In other embodiments, electrical connectors 800 can be male ZIF connectors or any suitable type of male or female electrical connector.

Figure 3:
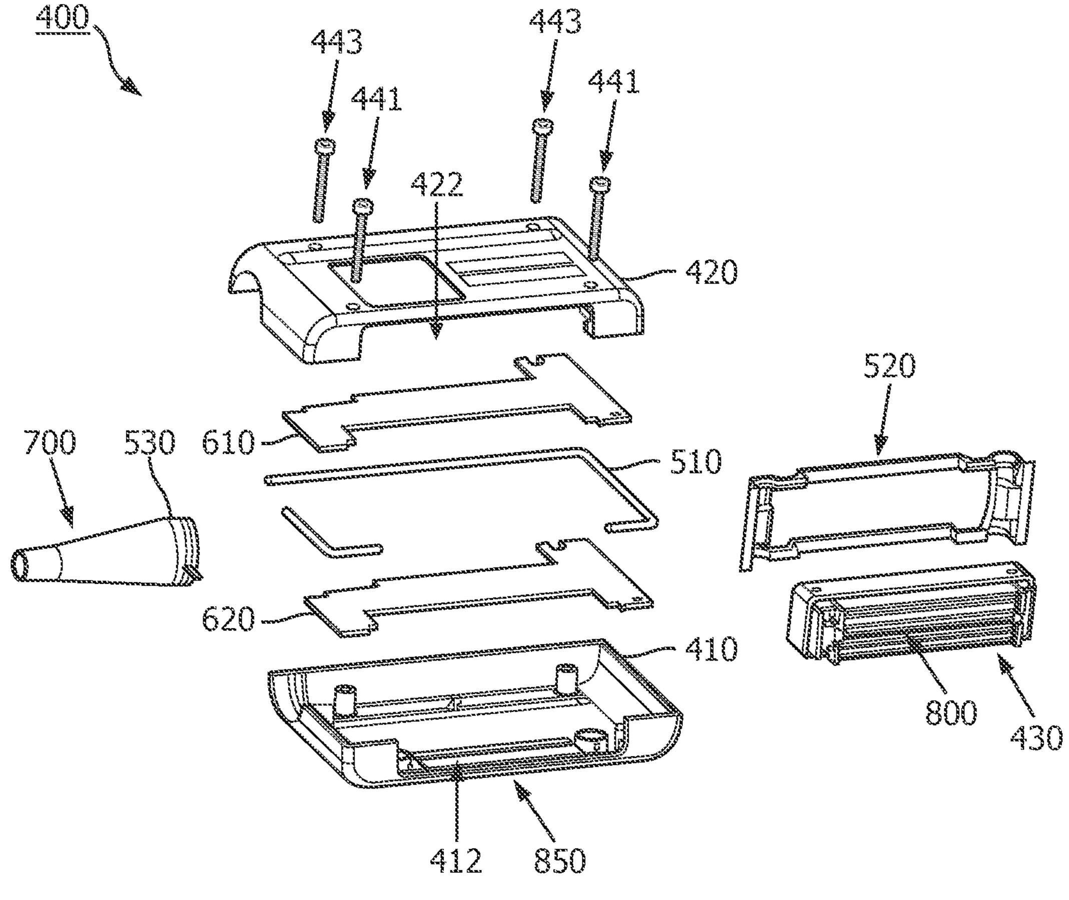
FIG. 3 is a diagrammatic exploded view of a connector assembly, according to aspects of the present disclosure.

FIG. 3 is a diagrammatic exploded view of the connector assembly 400, according to aspects of the present disclosure. In some embodiments, the connector assembly 400 includes a housing 410, a housing 420, a base housing 430, and an internal frame 440. The exterior of the body of the connector assembly 400 can be formed when the housing 410 and the housing 420 are coupled to one another. The base housing 430 houses one or more electrical connector 800. In some instances, the housing 410 can be referenced as a top housing, and the housing 420 can be referenced as a bottom housing. The base housing 430 can be referenced as a connector housing. In some embodiments, the top housing 410 is secured to the bottom housing 420 by a number of screws. In some instances, the top and bottom housings 410 and 420 are secured to one another by screws 441, 442, 443, and 444. In the illustrated embodiment, the top housing 410 and the bottom housing 420 have similar thicknesses along the direction of the screws 441, 442, 443, and 444. In other embodiments, one of the top and bottom housings 410 and 420 is thicker than the other along the direction of the screws 441, 442, 443, and 444. In some embodiments, the top housing 410 includes a base cutout 412 and the bottom housing 420 includes a base cutout 422. When the top housing 410 is secured to the bottom housing 420, the cutouts 412 and 422 together form an opening 850. The opening 850 is sized and shaped to receive the base housing 430. In some instances, the front and back housings 410 and 420 are formed of a metal or a metal alloy to shield off electromagnetic interferences.

In some embodiments, the connector assembly 400 includes an elastic seal member 520. The elastic seal member 520 surrounds the circumference of the base housing 430 and seals off the interface between the base housing 430, on the one hand, and the top and bottom housing 410 and 420. In some instances, elastic seal member 520 is concealed in a gap between the opening 850 and the circumference of the base housing 430 and therefore cannot be seen when the top housing 410 is secured to the bottom housing 420.

In some embodiments, the connector assembly 400 includes one or more printed circuit boards (PCBs). The PCBs can include one or more electronic components that provide signal conditioning and/or processing for the electrical signals representative of the imaging data obtained by the imaging assembly 902 (FIG. 1). In some instances, there are two printed circuit boards (PCBs) inside the connector assembly 400. As shown in FIG. 3, connector assembly 400 includes a PCB 610 and a PCB 620. The PCBs 610 and 620 are disposed between the top housing 410 and the bottom housing 420. In some instances, the PCBs 610 and 620 are planar and extend along two planes parallel to one another. As shown in FIG. 3, in some instances, each of the PCBs 610 and 620 includes a bracket-shaped cutout section adjacent to the cutouts 412 and 422.

In some embodiments, the connector assembly 400 includes one or more gaskets. As shown in FIG. 3, a gasket 510 is disposed between the top housing 410 and bottom housing 420 when the top housing 410 is secured to the bottom housing 420, for example, by screws 441, 442, 443, and 444. In some embodiments, the connector assembly 400 includes a conical cable housing 700. The conical cable housing 700 can serve as a cable strain relief to reduce mechanical stress on the cable 300. The conical cable housing 700 includes a distal end and a proximal end. The distal end of the conical cable housing 700 has a diameter smaller than the diameter of the proximal end. In some instances, a gasket 530 is installed on the proximal end of the conical cable housing 700. The gaskets 510 and 530 serve as barrier of humidity, disinfectants, and enzymatic cleaners and protect the PCBs 610 and 620 from being damaged by ingress of liquids. In some instances, gaskets 510 and 530 are made using stamping or die cutting process out of commercially available elastic sealing materials. In some instances, metal particles are incorporated into gaskets 510 and 530 to shield the connector assembly 400 from electromagnetic interferences.

Figure 4:
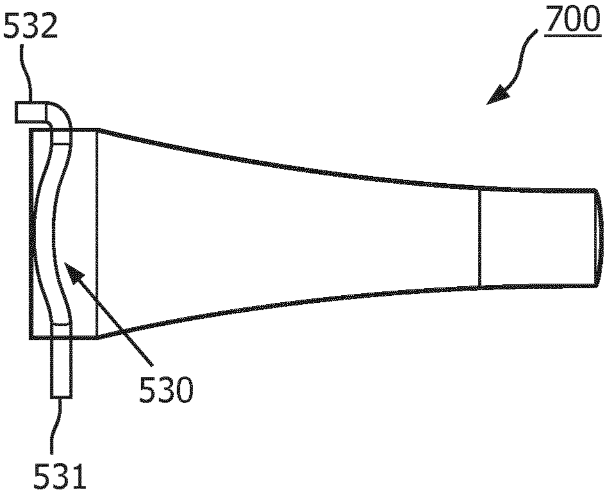
FIG. 4 is a diagrammatic schematic view of a conical cable housing and a gasket, according to aspects of the present disclosure.

FIG. 4 is a diagrammatic schematic view of the conical cable housing 700 and the gasket 530, according to aspects of the present disclosure. In some instances, the gasket 530 includes an extension 531 and an extension 532, both extending from the proximal end of the conical cable housing 700. In some embodiments, the extensions 531 and

532 are shaped and formed to engage the gasket 510 such that the gasket 530 is integrated with the gasket 510 or vice versa. The integration of the gaskets 510 and 530 are further illustrated in FIGS. 5A and 5B.

Figure 5:
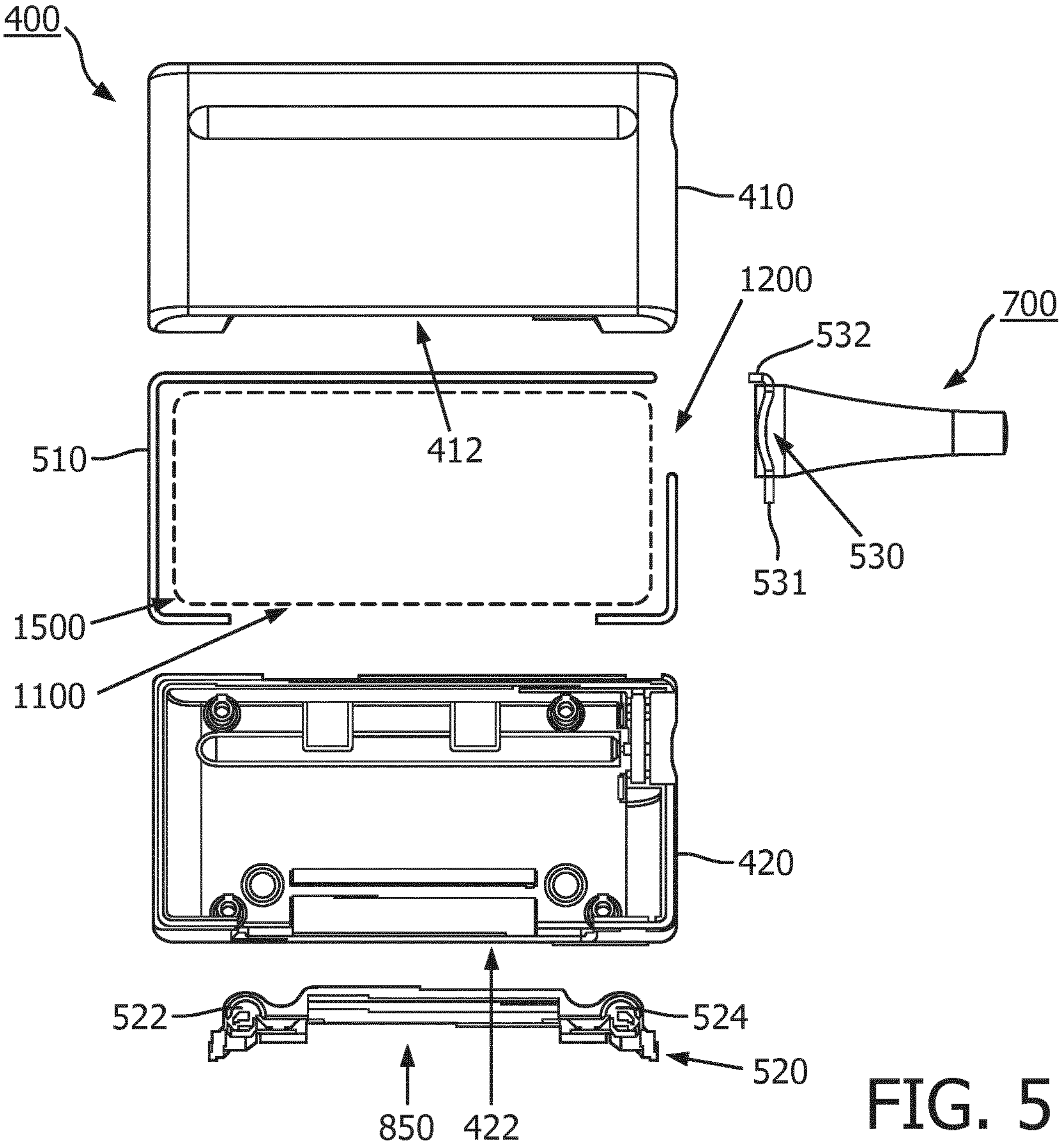
FIG. 5 is a diagrammatic perspective view of gaskets and elastic seal member of the connector assembly, according to aspects of the present disclosure.

FIG. 5 is a diagrammatic perspective view of gaskets 510 and 530 and the elastic seal member 520 of the connector assembly 400, according to aspects of the present disclosure. The gasket 510 is disposed between the top housing 410 and the bottom housing 420. In some instances, the gasket 510 includes a gap 1100 substantially coinciding with the cutouts 412 and 422, and therefore with the opening 850. In some instances, the gasket 510 includes another gap 1200 substantially coinciding with the extensions 531 and 532 extending from the proximal end of the conical cable housing 700. When the elastic seal member 520 is secured to the top and bottom housings 410 and 420 by screws 441 and 442, screw 441 threads through the bottom housing 420 and goes through a through hole 524 and screw 442 threads through the bottom housing 420 and goes through a through hole 522. What the elastic seal member 520 is so secured by screws 441 and 442, it overlaps with the gasket 510 at both ends of the gap 1100. As shown in FIG. 5A, the gasket 510 extends along a plane 1500. With the gap 1100 filled by the elastic seal member 520 and the gap 1200 filled by the gasket 530, the plane 1500 is sealed all around to provide a barrier of humidity, disinfectants, and enzymatic cleaners for the connector assembly 400 and render the connector assembly 400 waterproof and fully immersible in liquids.

Figure 6A:
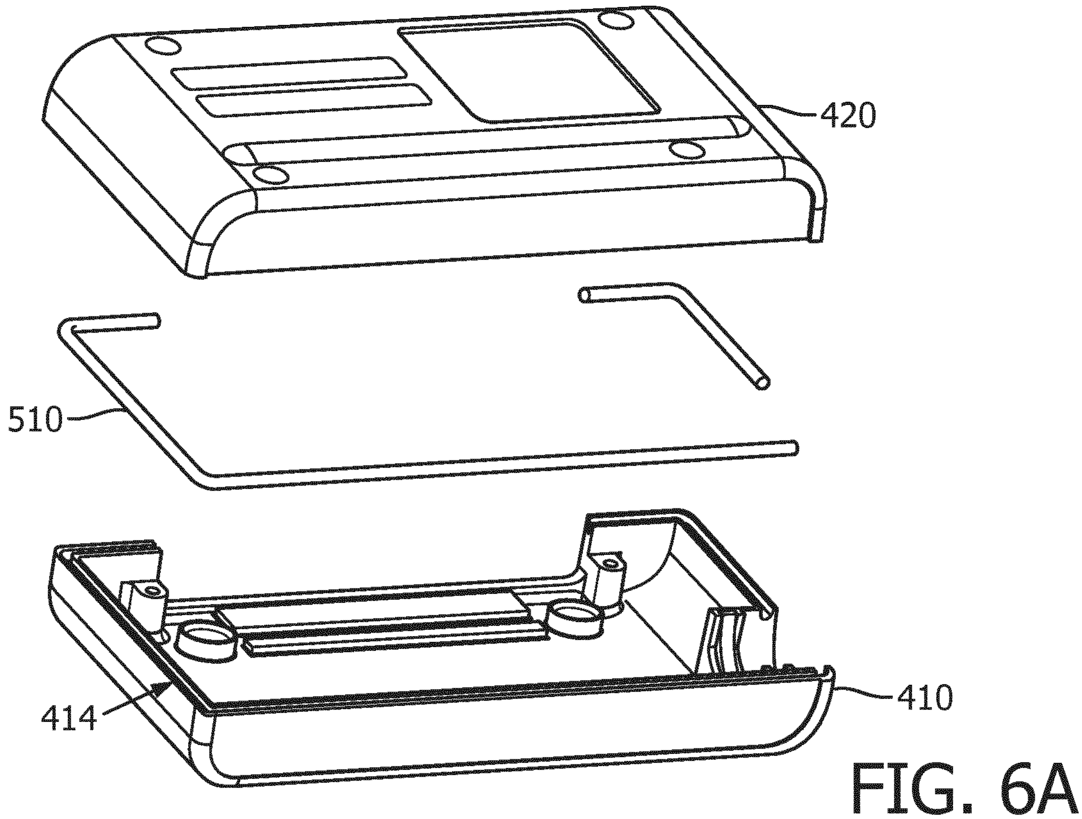
FIG. 6A is a diagrammatic perspective view of a top housing and a groove to receive a gasket, according to aspects of the present disclosure.
Figure 6B:
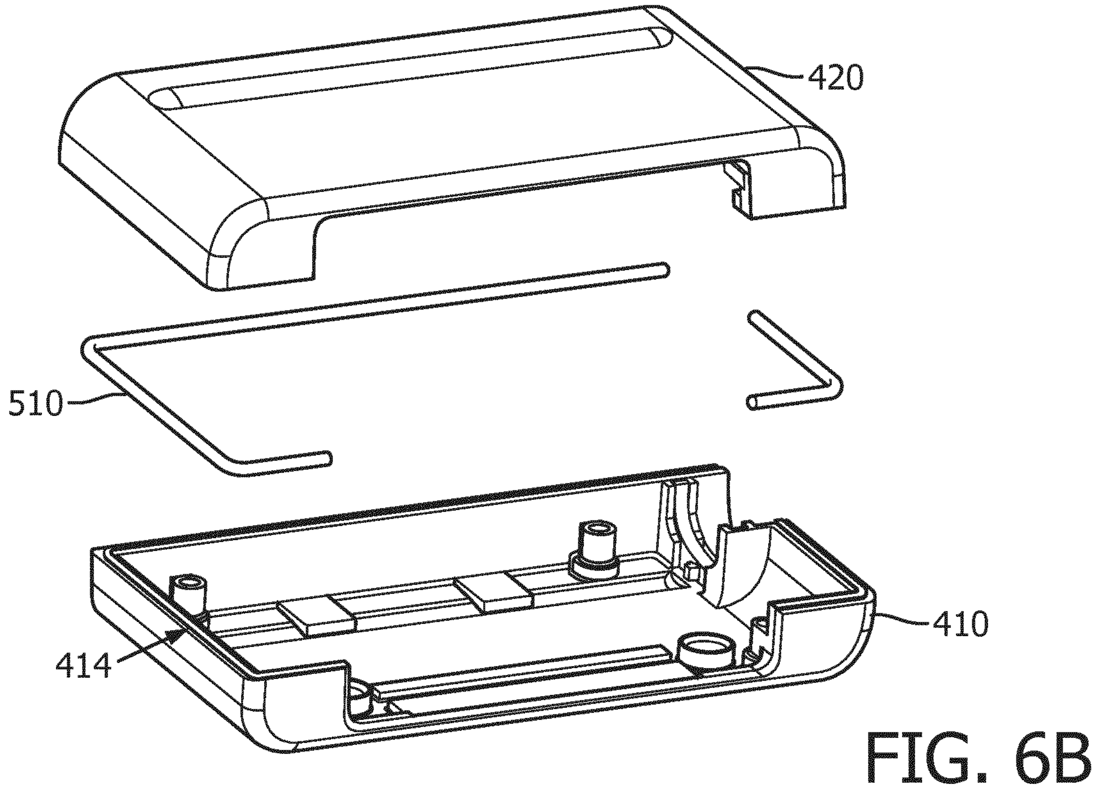
FIG. 6B is another diagrammatic perspective view of a bottom housing and a groove to receive a gasket, according to aspects of the present disclosure.

FIGS. 6A and 6B are diagrammatic perspective views of the top housing 410, the bottom housing and grooves to receive the gasket 510, according to aspects of the present disclosure. FIG. 6A can be described as illustrating a downward facing view, while FIG. 6B illustrates an upward facing view of the connector assembly 400. As described above, in some instances, the gasket 510 is disposed between the top housing 410 and the bottom housing 420. In some instances, a portion of the gasket 510 is received within a groove 414 of the top housing 410, as shown in FIG. 6A, and a portion of the gasket is received within a groove 424 of the bottom housing 420, as shown in FIG. 6B.

Figure 7:
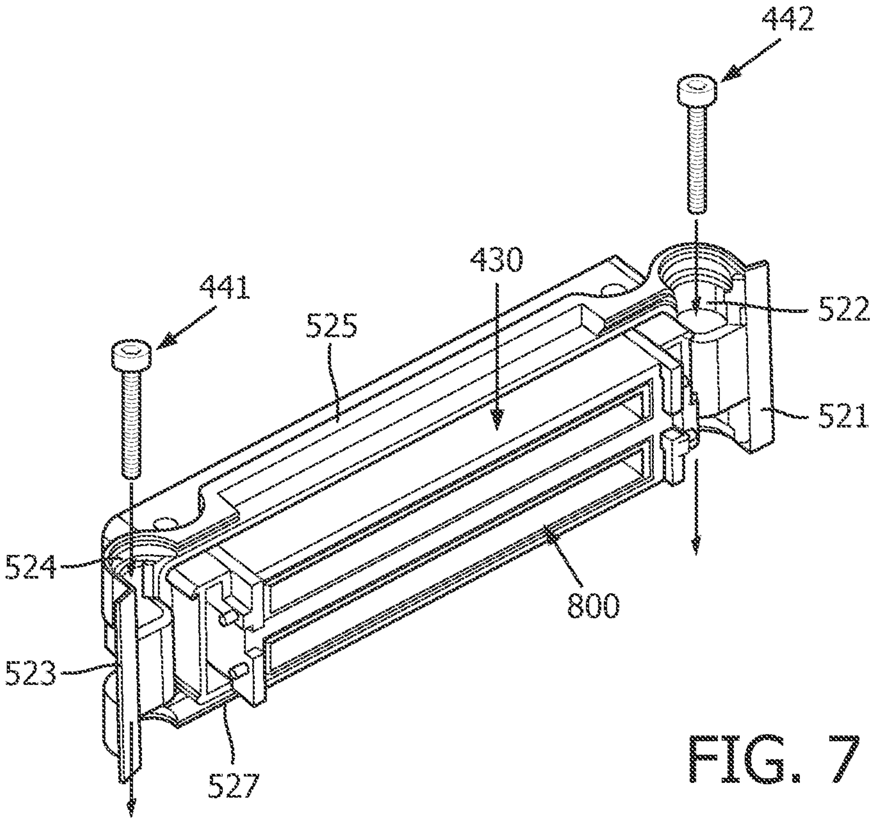
FIG. 7 is a diagrammatic perspective view of an elastic seal member surrounding a circumference of a base housing, according to aspects of the present disclosure.

FIG. 7 is a diagrammatic perspective view of the elastic seal member 520 surrounding a circumference of the base housing 430, according to aspects of the present disclosure. In some embodiments, the elastic seal member 520 includes a top edge 525 configured to engage the top housing 410 and a bottom edge 527 configured to engage the bottom housing 420. In some instances, the elastic seal member 520 includes a lip 521 adjacent to the through hole 522 and a lip 523 adjacent to the through hole 524. In some embodiments, the elastic seal member 520 surrounds the circumference of the base housing 430. In some instances, the base housing 430 has a cross section along the direction of the opening 850 and the cross section is rectangular in shape. The cross section of the base housing 430 includes two long sides and two short sides. In some embodiments, lip 521 is parallel and adjacent to one short side and lip 523 is parallel and adjacent to the other short side.

Figure 8:
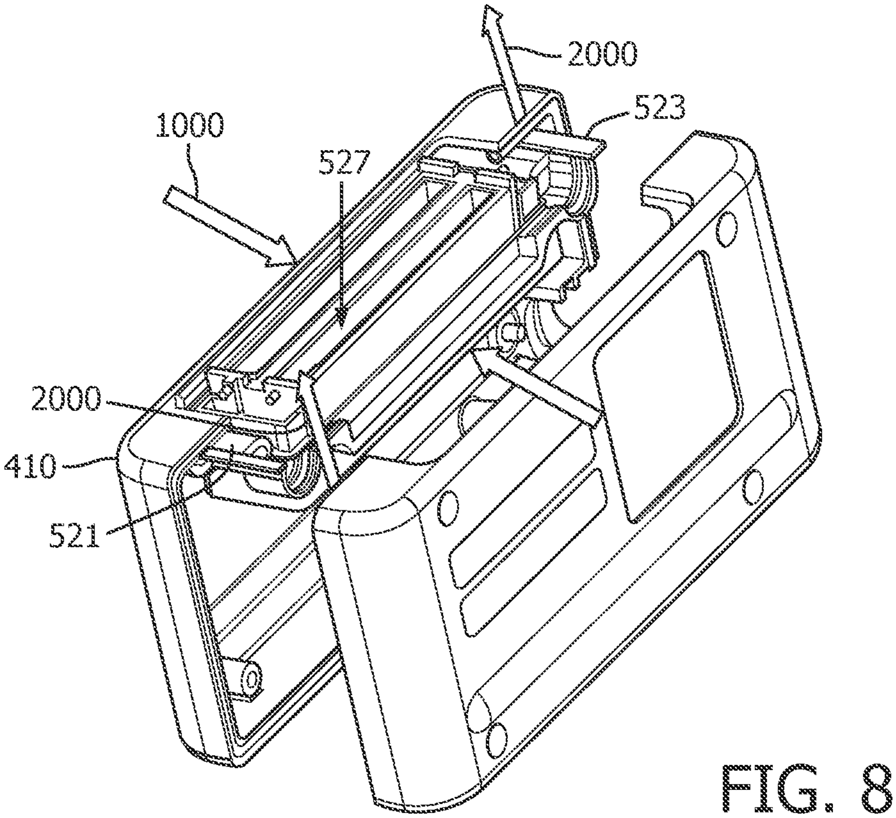
FIG. 8 is a diagrammatic perspective view of an elastic seal member disposed between a top housing and a bottom housing, according to aspects of the present disclosure.

That way, as shown in FIG. 8, when the top housing 410 is secured to the bottom housing 420, the top edge 525 (not shown) is pressed against the top housing 410 and the bottom edge 527 is pressed against the bottom housing 420. Consequently, in some instances, the elastic seal member 520 is compressed along a direction 1000. In addition, in the embodiments where the elastic seal member 520 includes the lips 521 and 523, when the top housing 410 is secured to the bottom housing 420, the lips 521 and 523 engages internal surfaces of both the top and bottom housings 410 and 420 along a direction 2000. The direction 1000 is different from the direction 2000. In some instances, the direction 1000 is perpendicular to the direction 2000.

Figure 9:
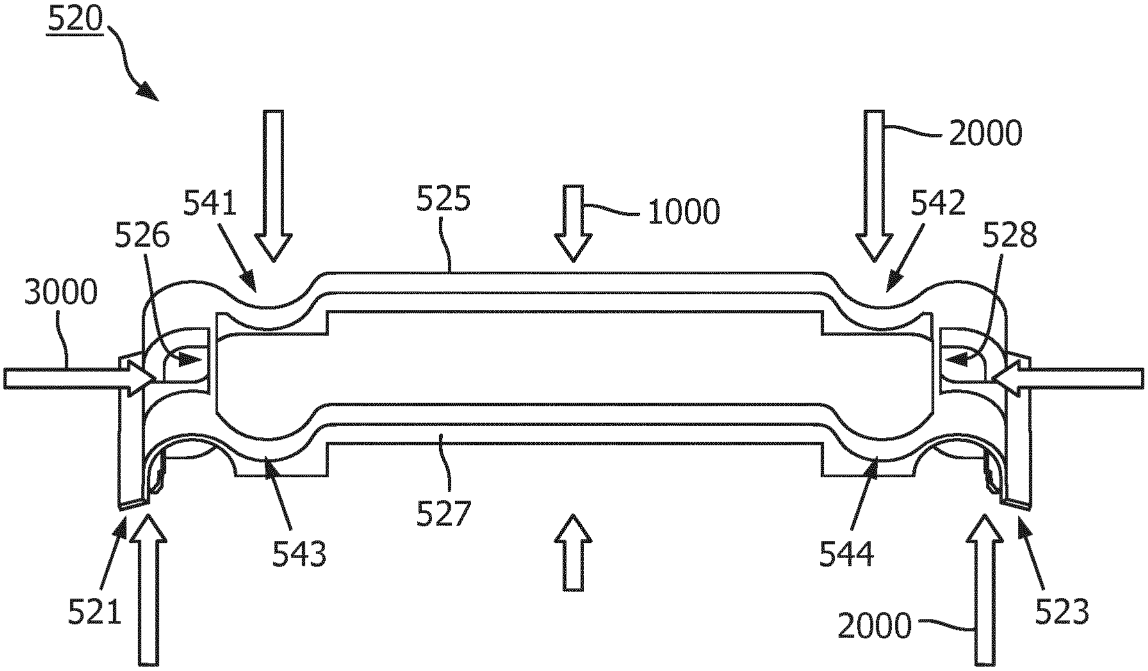
FIG. 9 is a diagrammatic perspective view of an elastic seal member, according to aspects of the present disclosure.

FIG. 9 is a diagrammatic perspective view of the elastic seal member 520, according to aspects of the present disclosure. In some embodiments, besides top edge 525, bottom edge 527, and lips 521 and 523, the elastic seal member 520 further includes a recess surface 526, a recess surface 528, and arches 541, 542, 543, and 544. In some embodiments, the elastic seal member 520 is compressed at all of the foregoing numbered locations. Specifically, the top edge 525 and the bottom edge 527 are compressed by the top and bottom housings 410 and 420 along the direction 1000. The tip 521 and 522 are compressed by the top and bottom housings 410 and 420 along the direction 2000. As will be further described below in conjunction with FIGS. 10, 11A, and 11B, the recess surfaces 526 and 528 are compressed by PCBs in a direction 3000 and the arches 541, 542, 543, and 544 are compressed in the direction 2000 by bosses coupled to internal surfaces of the top and bottom housings 410 and 420. The directions 1000, 2000 and 3000 are different from one another. In some instances, the directions 1000, 2000, and 3000 are perpendicular to one another. That is, in some instances, the elastic seal member 520 is compressed in three dimensions to serve as barrier of humidity, disinfectants, and enzymatic cleaners and protect the PCBs 610 and 620 from being damaged by ingress of liquids.

Figure 10:
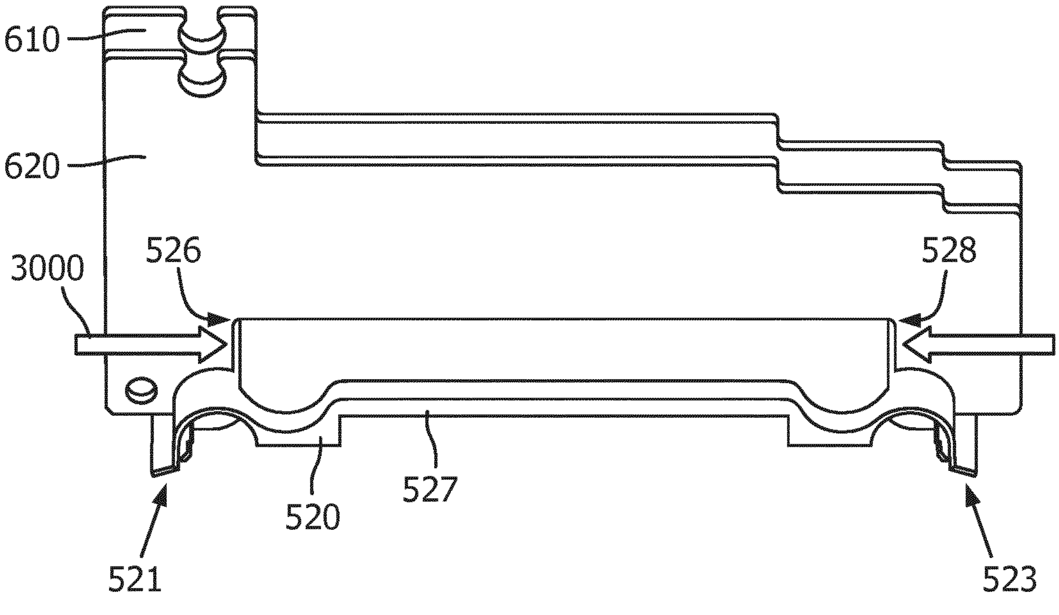
FIG. 10 is a diagrammatic perspective view of an elastic seal member and printed circuit boards, according to aspects of the present disclosure.

FIG. 10 is a diagrammatic perspective view of the elastic seal member 520 and PCBs 610 and 620, according to aspects of the present disclosure. In some instances, each of the PCBs 610 and 620 includes a bracket-shaped cutout section. When the PCBs 610 and 620 are arranged side-by-side as shown in FIG. 10, the bracket-shaped cutout sections of the PCBs 610 and 620 span across the elastic seal member 520 like a bridge and engage the recess surfaces 526 and 528 from either side of the elastic seal member 520 along the direction 3000. Arranged in that manner, the elastic seal member 520 is compressed by the PCBs 610 and 620 along the direction 3000. In some instances, to accommodate screw 441 going through the through hole 524 and screw 442 going through the through hole 522 (shown in FIG. 7), each of the PCBs 610 and 620 includes a pair of curved cutoffs on portions on both sides of the bracket-shaped cutout sections.

In some instances, the elastic seal member 520 is made using stamping or die cutting process out of commercially available elastic sealing materials. In some instances, metal particles are incorporated into seal member 520 to shield the connector assembly 400 from electromagnetic interferences.

Figure 11A:
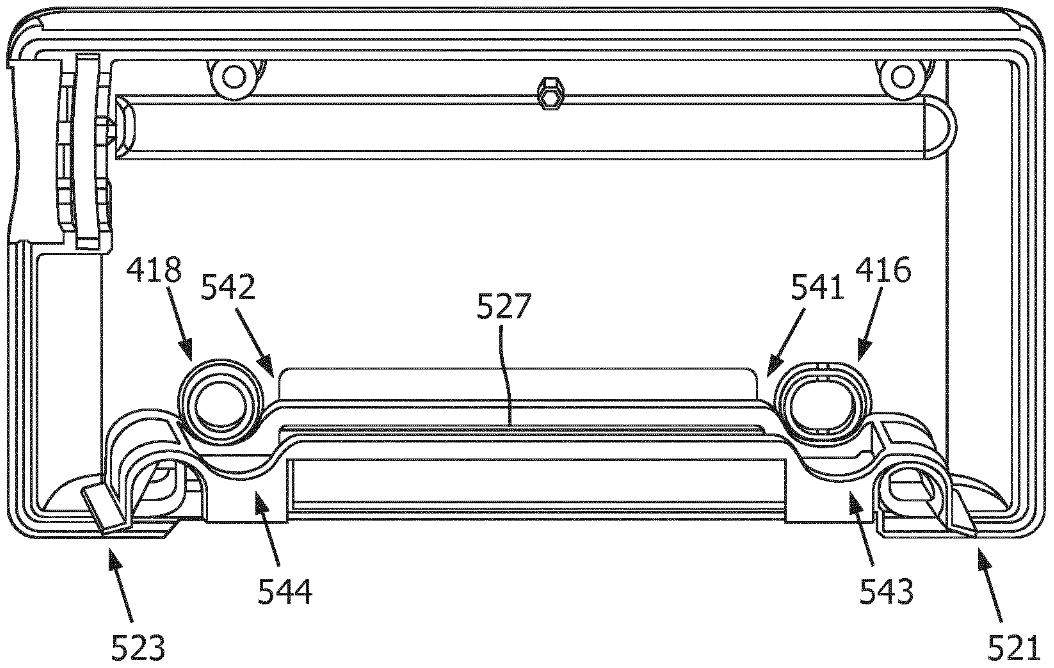
FIG. 11A is a diagrammatic perspective view of a top housing and an elastic seal member, according to aspects of the present disclosure.

FIG. 11A is a diagrammatic perspective view of the top housing 410 and the elastic seal member 520, according to aspects of the present disclosure. In some embodiments, the elastic seal member 520 includes an arch 541, an arch 542, an arch 543, and an arch 544. In some instances, the top and bottom housings 410 and 420 include internal surfaces and bosses protruding from the internal surfaces. In some embodiments, the top housing 410 includes a boss 416 and a boss 418 protruding from its internal surface. Both the bosses 416 and 418 are featured with a curvature that is identical or substantially similar to that of the arches 541 and 542. As shown in FIG. 11A, in some instances, when the top housing 410 is secured to the bottom housing 420, boss 416 is received in arch 541 and the boss 418 is received in arch 542. In some embodiments, bosses 416 and 418 can each include an indentation sized and shaped to receive a feature protruding from the base housing 430. In some instances, the feature is a screw securable to the base housing and the indentation is sized and shaped to receive a head of a screw. In those instances, the shape of the indentation depends on the shape of the head of the screw.

Figure 11B:
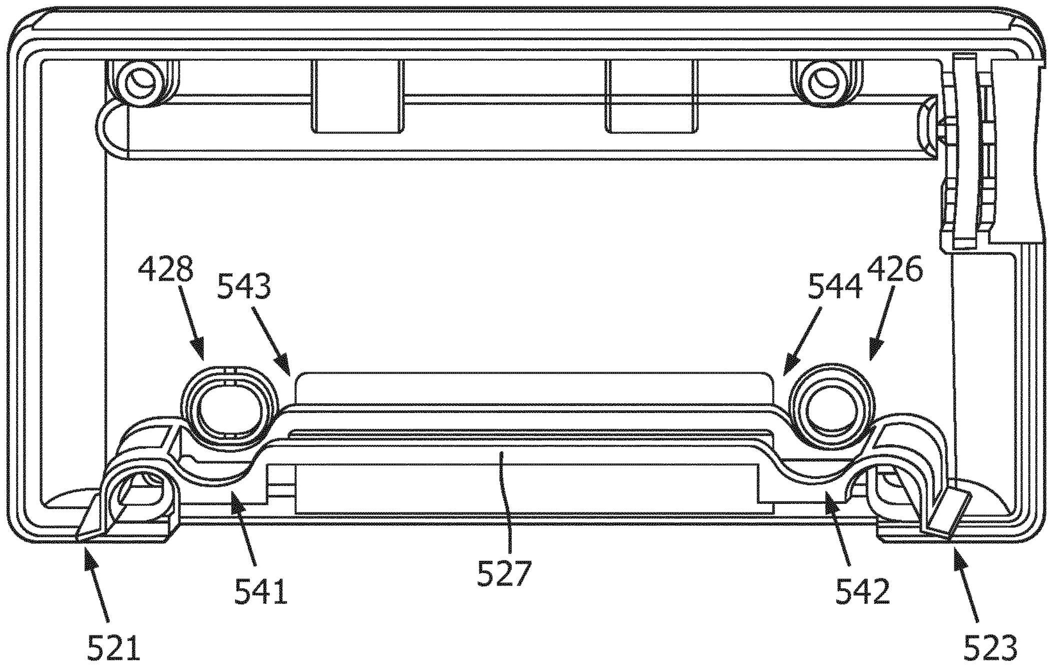
FIG. 11B is a diagrammatic perspective view of a bottom housing and an elastic seal member, according to aspects of the present disclosure.

Similarly, FIG. 11B is a diagrammatic perspective view of the bottom housing 420 and the elastic seal member 520, according to aspects of the present disclosure. In some embodiments, the bottom housing 420 includes a boss 426 and a boss 428 protruding from its internal surface. Both the bosses 426 and 428 are featured with a curvature that is identical or substantially similar to that of the arches 544 and 543. As shown in FIG. 11B, in some instances, when the top housing 410 is secured to the bottom housing 420, boss 426 is received in arch 544 and the boss 428 is received in arch 543. In some embodiments, bosses 426 and 428 can each include an indentation sized and shaped to receive a feature protruding from the base housing 430. In some instances, the feature is a screw securable to the base housing and the indentation is sized and shaped to receive a head of a screw. In those instances, the shape of the indentation depends on the shape of the head of the screw.

Figure 12:
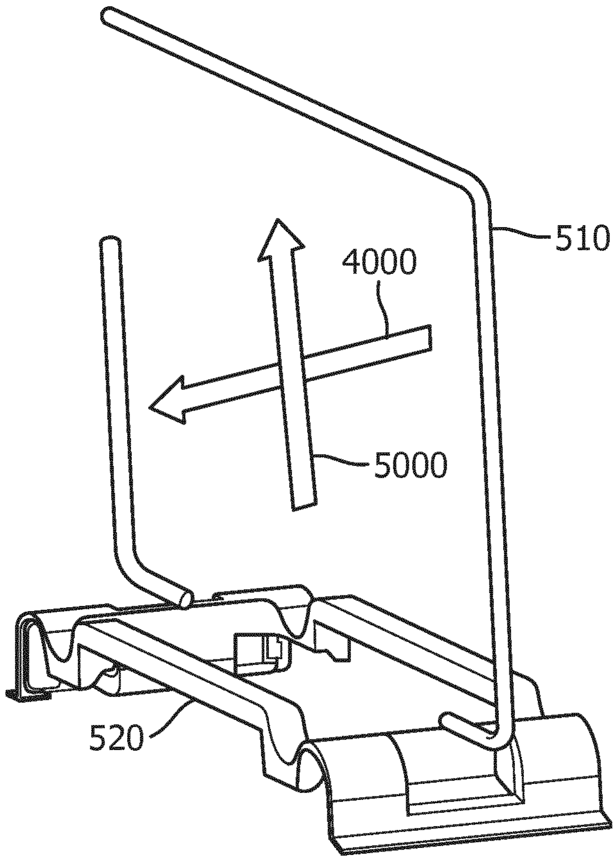
FIG. 12 is a diagrammatic perspective view of a first gasket and an elastic seal member, according to aspects of the present disclosure.

FIG. 12 is a diagrammatic perspective view of the gasket 510 and the elastic seal member 520, according to aspects of the present disclosure. In some instances, gasket 510 extends along a plane that has a normal direction 4000 and the elastic seal member 520 substantially extends along a plane that has a normal direction 5000. The direction 5000 is parallel to the direction of the opening 850 that is sized and shaped to receive the base housing 430. The direction 4000 is different from the direction 5000. In some instances, the direction 4000 is perpendicular to the direction 5000. In some instances, direction 4000 is parallel to direction 1000 in FIG. 8 and direction 5000 is parallel to direction 2000 in FIG. 8.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical imaging device connector assembly for connecting a medical imaging device to a terminal of a medical imaging system, the medical imaging device connector assembly comprising:

a top housing including a first base cutout;

a bottom housing configured to couple to the top housing, the bottom housing including a second base cutout;

a base housing positioned within the first and second base cutouts;

a plurality of printed circuit boards (PCBs) disposed between the top housing and the bottom housing;

an electrical connector positioned within the base housing; and an elastic seal member surrounding a circumference of the base housing, wherein when the top housing is coupled to the bottom housing, the elastic seal member is compressed by the plurality of PCBs in a first direction and by the top and bottom housings in a second direction perpendicular to the first direction to prevent fluid ingress.

2. The medical imaging device connector assembly of claim 1, wherein the top housing is coupled to the bottom housing by at least a first screw and a second screw.

3. The medical imaging device connector assembly of claim 2, wherein the elastic seal member comprises a first through hole sized and shaped to receive the first screw and a second through hole sized and shaped to receive the second screw.

4. The medical imaging device connector assembly of claim 1, wherein the elastic seal member comprises a top edge configured to engage the top housing and a bottom edge configured to engage the bottom housing.

5. The medical imaging device connector assembly of claim 4, wherein the base housing comprises two short sides and two long sides, wherein the elastic seal member comprises a first lip parallel and adjacent to one short side and a second lip parallel and adjacent to the other short side, each of the first and second lips being configured to engage the top and the bottom housings simultaneously.

6. The medical imaging device connector assembly of claim 1, further comprising a gasket, wherein the top housing includes a first groove configured to receive a portion of the gasket, wherein the bottom housing includes a second groove configured to receive a portion of the gasket, and wherein the gasket is disposed between the first groove and the second groove when the top housing is secured to the bottom housing.

7. The medical imaging device connector assembly of claim 6, wherein the elastic seal member extends along a first plane having a first normal direction and the gasket extends along a second plane having a second normal direction, the first normal direction being perpendicular to the second normal direction.

8. The medical imaging device connector assembly of claim 1, wherein the elastic seal member comprises conductive particles.

9. The medical imaging device connector assembly of claim 1, wherein the electrical connector is a zero insertion force (ZIF) connector.

10. The medical imaging device connector assembly of claim 9, wherein the electrical connector is a female ZIF connector configured to be electrically connected to a male ZIF connector.

11. The medical imaging device connector assembly of claim 10, wherein the terminal of the medical imaging system comprises the male ZIF connector.

12. The medical imaging device connector assembly of claim 6, further comprising a conical cable housing having a proximal end and a distal end, the proximal end having a first outer diameter, the distal end having a second outer diameter smaller than the first outer diameter.

13. The medical imaging device connector assembly of claim 12, wherein the gasket is a first gasket and the conical cable housing comprises a second gasket, the second gasket including a first extension and a second extension extending from the proximal end of the conical cable housing.

14. The medical imaging device connector assembly of claim 13, wherein when the top housing is coupled to the bottom housing, the first and second extensions of the second gasket engage the first gasket.

15. The medical imaging device connector assembly of claim 1, wherein the top housing comprises an internal surface and a boss coupled to the internal surface of the top housing, wherein the bottom housing comprises an internal surface and a boss coupled to the internal surface of the bottom housing, wherein the boss on the top housing and the boss on the bottom housing engage and strain the elastic seal member.

16. A system, comprising:

a medical imaging device, comprising:

a flexible elongate member comprising a proximal portion and a distal portion;

an imaging assembly at the distal portion; and a connector assembly at the proximal portion and configured to connect to a terminal of a medical imaging system, the connector assembly comprising:

a top housing including a first base cutout;

a bottom housing configured to couple to the top housing, the bottom housing including a second base cutout;

a base housing positioned within the first and second base cutouts;

a plurality of printed circuit boards (PCBs) disposed between the top housing and the bottom housing;

an electrical connector positioned within the base housing; and an elastic seal member surrounding a circumference of the base housing, wherein when the top housing is coupled to the bottom housing, the elastic seal member is compressed by the plurality of PCBs in a first direction and by the top and bottom housings in a second direction perpendicular to the first direction to prevent fluid ingress.

17. The system of claim 16, further comprising:

a medical imaging system.

* * * * *